(12) United States Patent
Audigier et al.

(10) Patent No.: US 9,846,765 B2
(45) Date of Patent: Dec. 19, 2017

(54) SYSTEM AND METHOD FOR PATIENT SPECIFIC MODELING OF LIVER TUMOR ABLATION

(71) Applicants: Chloe Audigier, Valbonnes (FR); Tommaso Mansi, Plainsboro, NJ (US); Viorel Mihalef, North Brunswick, NJ (US); Ali Kamen, Skillman, NJ (US); Dorin Comaniciu, Princeton, NJ (US); Puneet Sharma, Monmouth Junction, NJ (US); Saikiran Rapaka, Ewing, NJ (US); Herve Delingette, Sophia-Antipolis (FR); Nicholas Ayache, Nice (FR)

(72) Inventors: Chloe Audigier, Valbonnes (FR); Tommaso Mansi, Plainsboro, NJ (US); Viorel Mihalef, North Brunswick, NJ (US); Ali Kamen, Skillman, NJ (US); Dorin Comaniciu, Princeton, NJ (US); Puneet Sharma, Monmouth Junction, NJ (US); Saikiran Rapaka, Ewing, NJ (US); Herve Delingette, Sophia-Antipolis (FR); Nicholas Ayache, Nice (FR)

(73) Assignees: Siemens Healthcare GmbH, Erlangen (DE); INRIA, Sophia Antipolis (FR)

( * ) Notice: Subject to any disclaimer, the term of this patent is extended or adjusted under 35 U.S.C. 154(b) by 800 days.

(21) Appl. No.: 14/071,688

(22) Filed: Nov. 5, 2013

(65) Prior Publication Data
US 2014/0136174 A1 May 15, 2014

Related U.S. Application Data

(60) Provisional application No. 61/724,567, filed on Nov. 9, 2012.

(51) Int. Cl.
| G06F 19/00 | (2011.01) |
| G06F 19/10 | (2011.01) |
| G09B 23/30 | (2006.01) |

(52) U.S. Cl.
CPC ...... *G06F 19/3437* (2013.01); *G06F 19/3481* (2013.01); *G09B 23/30* (2013.01)

(58) Field of Classification Search
None
See application file for complete search history.

(56) References Cited

U.S. PATENT DOCUMENTS

| 8,267,927 B2 | 9/2012 | Dalal et al. |
| 8,295,913 B2 | 10/2012 | Haras |
| 2008/0300588 A1 | 12/2008 | Groth et al. |
| 2009/0124896 A1 | 5/2009 | Haras |
| 2009/0142740 A1 | 6/2009 | Liang et al. |
| 2009/0221999 A1 | 9/2009 | Shahidi |
| 2011/0015628 A1 | 1/2011 | Dalal et al. |
| 2011/0196385 A1 | 8/2011 | Altrogge et al. |
| 2011/0251607 A1 | 10/2011 | Kruecker et al. |
| 2013/0158577 A1 | 6/2013 | Mahon et al. |
| 2014/0022250 A1 | 1/2014 | Mansi et al. |

FOREIGN PATENT DOCUMENTS

| CN | 101563041 A | 10/2009 |
| CN | 101859341 A | 10/2010 |
| CN | 102264315 A | 11/2011 |
| CN | 102346811 A | 2/2012 |

OTHER PUBLICATIONS

Payne et al. (Phil. Trans. R. Soc. A (2011) vol. 369, pp. 4233-4254).*
Peng et al. (International Journal of Heat and Mass Transfer (2011) vol. 54, pp. 2100-2109).*
Grady (IEEE Transactions on Pattern Analysis and Machine Intelligence (2006) vol. 28, pp. 1768-1783).*
O'Neill et al. (Annals of Biomedical Engineering (2011) vol. 39, pp. 570-579).*
Chen et al. (IEEE Transactions on Biomedical Engineering (2009) vol. 56, pp. 237-245).*
Reider et al. (IEEE Transactions on Visualization and Computer Graphics (2011) vol. 17, pp. 1812-1821).*
Santos et al. (BioMedical Engineering OnLine (2008) vol. 7, e-pp. 1-11).*
Rapaka, et al., "LBM-EP: Lattice-boltzmann method for fast cardiac electrophysiology simulation from 3d images", In: Medical Image Computing and Computer-Assisted Intervention MICCAI, 2012, pp. 33-40, vol. 7511, Springer Berlin Heidelberg.
Chinese Office Action dated Jun. 16, 2017 in corresponding Chinese Application No. 201310757217.2.

* cited by examiner

*Primary Examiner* — Lori A Clow (57) ABSTRACT

A method and system for tumor ablation planning and guidance based on a patient-specific model of liver tumor ablation is disclosed. A patient-specific anatomical model of the liver and circulatory system of the liver is estimated from 3D medical image data of a patient. Blood flow in the liver and the circulatory system of the liver is simulated based on the patient-specific anatomical model. Heat diffusion due to ablation is simulated based on a virtual ablation probe position and the simulated blood flow in the liver and the venous system of the liver. Cellular necrosis in the liver is simulated based on the simulated heat diffusion. A visualization of a simulated necrosis region is generated and displayed to the user for decision making and optimal therapy planning and guidance.

25 Claims, 6 Drawing Sheets

ALGORITHM 1 COMPUTATIONAL MODEL OF RFA

- 402 → 1: ESTIMATE PATIENT-SPECIFIC MODEL OF LIVER ANATOMY
- 404 → 2: COMPUTE 3D BLOOD FLOW AND $\varphi i$ AND INLET PRESSURES $\bar{p}_i$ IN HEPATIC VEIN
- 406 → 3: COMPUTE PORTAL VEIN UPSTREAM PRESSURES $p^+$ BY FITTING DARCY'S MODEL TO HEPATIC VEIN DOWNSTREAM PRESSURE $\bar{p}_i$ AND FLOW $\varphi i$
- 408 → 4: COMPUTE 3D BLOOD FLOW IN PORTAL VEIN
- 5: WHILE $t < t_{end}$ do
- 6: $t \leftarrow t + \Delta t$
- 410 → 7: UPDATE TEMPERATURE $T$ USING PENNES MODEL IN THE LARGE VESSELS, WULFF-KLINGER MODEL ELSEWHERE
- 412 → 8: UPDATE CELL-STATE

SYSTEM AND METHOD FOR PATIENT SPECIFIC MODELING OF LIVER TUMOR ABLATION

This application claims the benefit of U.S. Provisional Application No. 61/724,567, filed Nov. 9, 2012, the disclosure of which is herein incorporated by reference.

BACKGROUND OF THE INVENTION

The present invention relates to ablation planning, and more particularly to therapy planning and guidance based on a patient-specific model of liver tumor ablation using medical imaging data.

Ablation is one option for cancer treatment. In spite of recent advances in cancer therapy, treatment of primary and metastatic tumors of the abdomen remains a significant challenge. Hepatocellular carcinoma (HCC) for example is one the most common malignancies encountered throughout the world (e.g., >1 million cases per year). In the U.S. alone, 1 in 153 individuals will develop HCC with reported 5-year survival rates of less than 15%.

For both primary liver cancer and hepatic metastases, liver resection (partial hepatectomy) is the current preferred option in patients having confined disease. In selected cases of early HCC, total hepatectomy with liver transplantation may also be considered. Unfortunately, less than 25% of patients with primary or secondary liver cancer are candidates for resection or transplantation, primarily due to tumor type, location, or underlying liver disease. Consequently, increasing interest has been focused on ablative approaches for the treatment of unresectable liver tumors. Rather than extirpation, this technique uses complete local in situ tumor destruction. A variety of methods have been employed to locally ablate tissue. Radiofrequency ablation (RFA) is the most commonly used, but other techniques are also used, including ethanol injection, cryo-therapy, irreversible electroporation, and microwave ablation.

The RFA procedure is performed by placing a probe within the target area, the tumor, in the liver parenchyma. Electrodes at the tip of the probe create heat, which is conducted into the surrounding tissue, causing coagulative necrosis at temperatures between 50° C. and 100° C. In addition to increasing the number of patients eligible for curative therapy of liver cancer in unresectable patients, local tissue ablation has a significant advantage as ablation may be performed using a minimally invasive approach, including percutaneously and laparoscopically.

To place the probe at the target location, the physician relies on intra-operative imaging techniques, such as ultrasound. However, the success of the procedure depends on the optimal placement of the probe and heat delivery. Different placements may have different results. The success of ablation is further challenged by the hepatic blood vessels that dissipate heat, thus potentially reducing RFA efficiency.

BRIEF SUMMARY OF THE INVENTION

The present invention provides a method and system for patient-specific modeling of liver tumor ablation. Embodiments of the present invention model the effects of ablation including heat diffusion, cellular necrosis, and blood flow through the vessels and liver. Starting from a preoperative medical image of a patient, such as a computed tomography (CT) or magnetic resonance imaging (MRI) image, the patient-specific geometry of the liver and venous system are automatically estimated. The vessel structure for the patient is accounted for as a heat sink in the model of biological heat transfer. The biological heat transfer model is coupled to a computational fluid dynamics solver to accurately take into account the effect of blood circulation on the dissipated heat. A cellular necrosis model is employed to simulate cell death due to over-heating and a simulated necrosis area can be visualized.

In one embodiment of the present invention, a patient-specific anatomical model of the liver and venous system of the liver is estimated from 3D medical image data of a patient. Blood flow in the liver and the venous system of the liver is simulated based on the patient-specific anatomical model. Heat diffusion due to ablation is simulated based on a virtual ablation probe position and its operating parameters and the simulated blood flow in the liver and the venous system of the liver. Cellular necrosis in the liver is simulated based on the simulated heat diffusion. A visualization of a simulated necrosis region and temperature map is generated.

These and other advantages of the invention will be apparent to those of ordinary skill in the art by reference to the following detailed description and the accompanying drawings.

DETAILED DESCRIPTION

The present invention relates to patient-specific modeling and simulation of liver tumor ablation using medical imaging data. Embodiments of the present invention are described herein to give a visual understanding of the methods for patient-specific modeling and simulation using medical imaging data. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention utilize a computational framework for patient-specific planning and guidance of radio-frequency ablation. Starting from a preoperative 3D medical image, such as a computed tomography (CT) image, the geometry of the liver and the venous system is automatically estimated using an efficient machine algorithm. A bio-heat equation is then solved to obtain a temperature profile throughout the liver over time. Tissue parameters are updated at every time step of the computation according to a cellular necrosis model.

Figure 1:
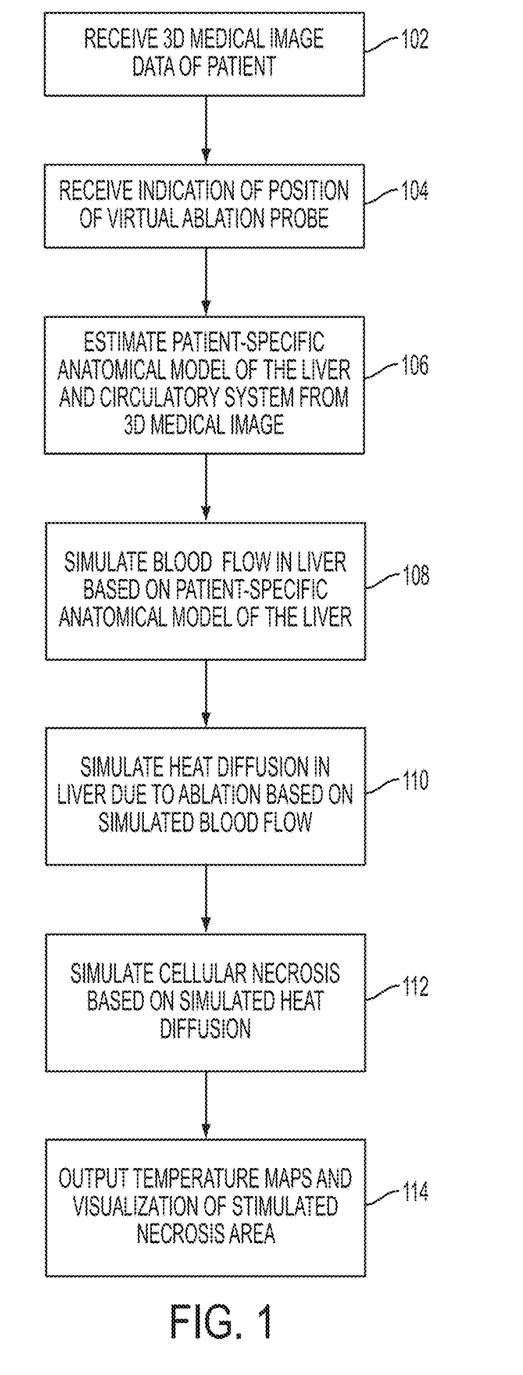
FIG. 1 illustrates a method for patient-specific modeling of liver tumor ablation according to an embodiment of the present invention.

FIG. 1 illustrates a method for patient-specific modeling of liver tumor ablation according to an embodiment of the present invention. The method of FIG. 1 transforms medical image data representing a patient's liver anatomy to provide patient-specific simulation of liver tumor ablation. It is to be understood that the method of FIG. 1 is not limited to the liver and can be similarly applied to other target organs as well. At step 102, pre-operative 3D medical image data of at least of liver region of a patient is received. The pre-operative 3D image data can be acquired using any type of medical imaging modality, such as computed tomography (CT), three-dimensional rotational angiography, magnetic resonance imaging (MRI), ultrasound (US), positron emission tomography (PET), etc., provided that the liver is entirely visible in the medical image data. The medical image data can be received directly from an image acquisition device, such as a CT scanner, a C-arm image-acquisition device, an MRI scanner, or an US scanner, or the pre-operative cardiac image data can be received by loading previously stored cardiac image data of the patient. In a possible embodiment, a computed tomography, fluoroscopy, x-ray, or CT angiography system may be used to acquire the medical image data. The patient may ingest or be injected with a contrast agent that is generally opaque to x-rays. The contrast agent collects or is in the circulatory system, so vessels contrast with tissue. Any scanning sequence or approach may be used, such as CT angiography modes or rotational angiography to generate the pre-operative 3D medical image data.

At step 104, an indication of a position of a virtual ablation probe and its operational parameters are received. In one embodiment, a user indication of a placement position of the ablation probe is received. The ablation is to occur near or in a lesion (e.g., tumor) or other region of tissue. Given anatomy, type of ablation, type of ablation device, or other limitations, the placement in the tissue may be limited. The user may indicate a possible placement of the ablation probe by selecting a location or locations in the pre-operative medical image data. For example, a location in a multi-planar reconstruction of the patient can be selected by a user using an input device, such as a mouse, touch screen, etc.

In a possible implementation, multiple positions of the ablation probe may be provided. For example, the user may indicate a sequence of placements for simulating sequential ablation operations or applications. In this case, the sequence is simulated by repeating steps 108-114 of FIG. 1 for each sequential probe position using the results from the previous run. Using the modeling of cellular necrosis in step 112, the changed tissue properties for various locations may be considered during the subsequent runs. Sequential placement may be used for larger tumors, where the single probe placement does not provide sufficient coverage of the thermal dose to the tumor. In another possible implementation, the user may indicate multiple placements for simulating ablation using multiple devices at a same time. The aggregated thermal dose is computed based on a single simulation run.

In an alternative embodiment, the user does not indicate placement. Instead, the position is selected automatically based on the image data, such as by identifying a center of the tumor. Various possible placements may be automatically identified and tested with separate simulations.

In addition to the position of the virtual ablation probe, the user may also input a spatial extent of the ablation probe, the type of ablation, duration, a desired dose, an indication of the spatial extent of the tumor, an indication of a location in the tumor, an amount of power for ablation, a type of ablation device, a sequence of power, and/or other characteristic of the ablation or tissue. Various inputs may be automated. Instead of user input, a processor provides the information.

At step 106, a patient-specific anatomical model of the liver and the circulatory system in the liver is estimated from the 3D medical image data. The patient-specific anatomical model is a detailed anatomical model of the patient's liver parenchyma, tumors, hepatic vein, portal vein, and arteries. The 3D surface of the liver may be segmented automatically from the 3D medical image data. In one embodiment, the patient-specific anatomical model is semi-automatically estimated from the CT data using a graph theory approach, such as random walker segmentation. For each structure (parenchyma, tumors, hepatic vein, portal vein, arteries), the user defines seeds inside and outside the area of interest. Then, the random-walker algorithm automatically estimates the boundary of the structure. The process may be refined by the user, interactively, if necessary. Next, the resulting segmentations are merged into a multi-label mask image, which is then used to generate a tetrahedral multi-domain mesh.

Figure 2:
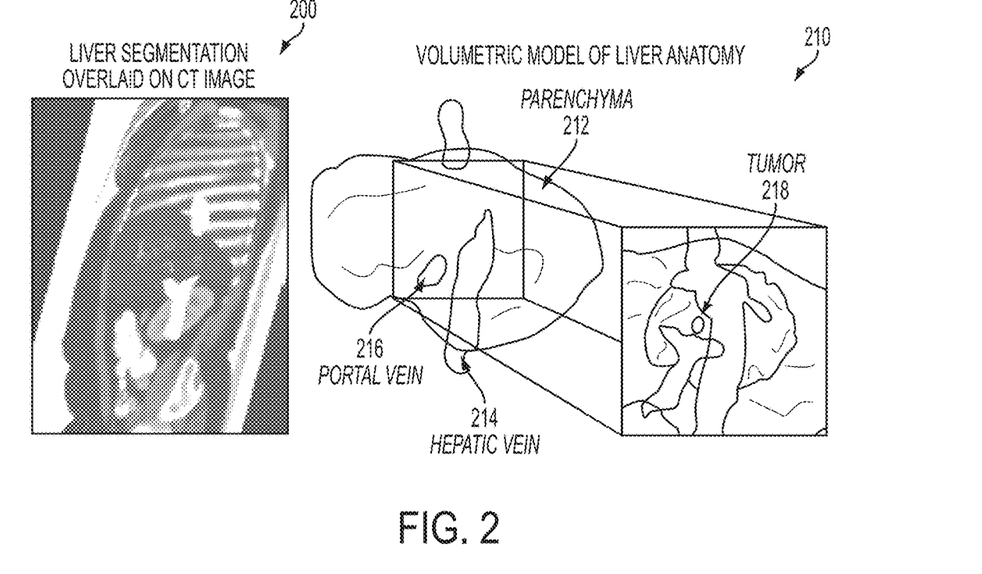
FIG. 2 illustrates exemplary results for estimating a patient-specific anatomical model of the liver.

FIG. 2 illustrates exemplary results for estimating a patient-specific anatomical model of the liver. As shown in FIG. 2, image 200 shows the liver segmentation 102 overlaid on a CT image. Image 210 shows the tetrahedral volume mesh generated from the liver segmentation, including the parenchyma 212, hepatic vein 214, portal vein 216, and a segmented tumor 218.

Returning to FIG. 1, at step 108, blood flow in the liver is simulated based on the patient-specific anatomical model of the liver and venous system. The blood flow through the venous system of the liver acts as a heat sink in diffusing the heat applying by the ablation probe. The blood flow in the patient-specific anatomic model is simulated in order to provide a personalized modeling of the heat sink due to the blood flow. Locations of the vessels in the tissue region, the size of the vessels, and/or other vessel characteristics are used to model the heat sink characteristics in the region of interest. The characteristics may be extracted from the segmented vessel information in the patient-specific anatomical model of the liver.

Figure 3:
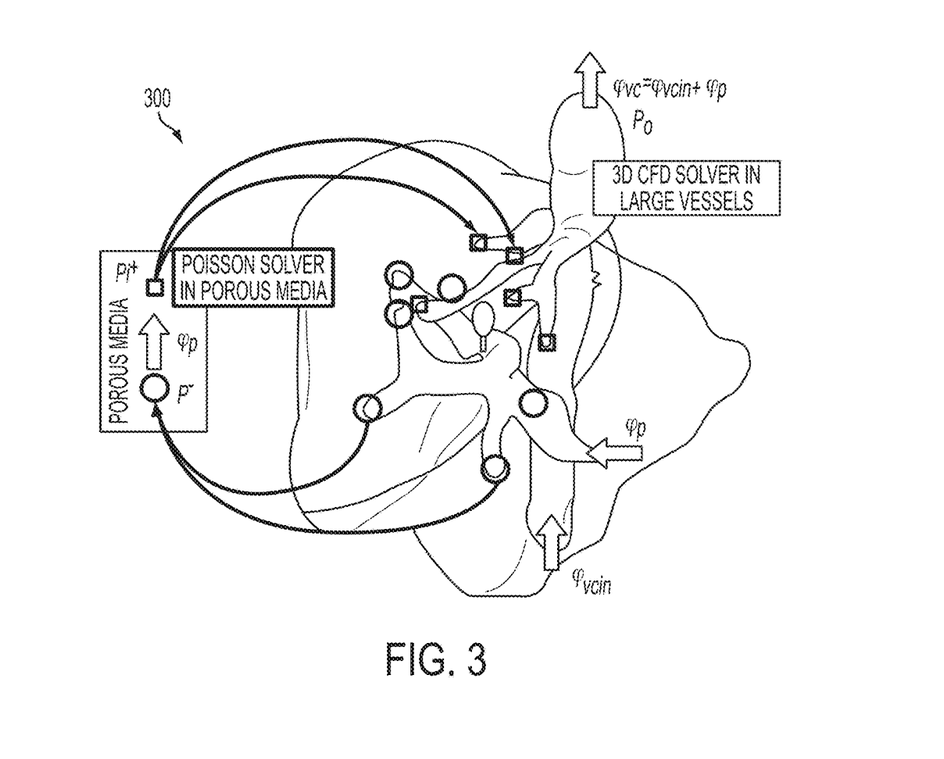
FIG. 3 illustrates an exemplary computational fluid dynamics (CFD) model of the hepatic venous circulatory system.

The liver is treated as a porous media, so solving Darcy's law provides a velocity field throughout the organ that is used in the advection part of the heat transfer model. The blood velocity v inside the parenchyma is calculated according to Darcy's law: $v=-k/(\mu e^{2/3})\text{del}\cdot p$, where p is the pressure within the parenchyma and $\mu$ is the dynamic viscosity of the blood flow. This amounts to solving the Laplace equation $\text{del}\cdot((-k/(\mu e^{2/3})\text{del}\cdot p)=0$. At the border of the liver, Neumann boundary conditions are employed as no or little flow leaks outside the liver, whereas at the tip of portal and hepatic veins, Dirichlet boundary conditions are applied. Since the pressures cannot be estimated in-vivo, a computational fluid dynamics (CFD) model of the hepatic venous circulation system is used to estimate the pressures. FIG. 3 illustrates an exemplary CFD model of the hepatic venous circulatory system 300. As shown in FIG. 3, arrows denote blood flow, circles denote portal vessel tips, and squares denote hepatic vessel tips. Let $\phi_{vcin}$ be the vena cava inflow, $\phi_p$ the portal vein inflow, and $\phi_{vc}$ be the vena cava outflow, which in virtue of conservation of mass is equal to $\phi_{vcin}+\phi_p$.

The hepatic artery may be ignored or included as well. A small pressure is assumed to exist at the outlet of the vena cava (e.g., $p_0=1$ mmHg).

The blood flow and pressure distribution are computed within the vena cava (302 in FIG. 3) using three-dimensional computational fluid dynamics (e.g., using unsteady incompressible Navier-Stokes equations with viscous terms). The blood is modeled as a Newtonian fluid with pre-specified density (e.g., density=1.05 g/cm$^3$) and viscosity (e.g., viscosity=0.004 Pa s). The parameters may be different from one patient to another. A plug profile velocity field is applied at the inlets (squares in FIG. 3), computed from the outflow $\phi_p$ and the cross-sectional area of each inlet. From the computational fluid dynamics computation, the downstream pressures $p_i^-$ for each inlet of the vena cava is provided. The upstream pressure $p^+$ at each of the portal vein tips (circles in FIG. 3) is assumed constant such that the computed perfused flow through the vena cava inlets matches the three-dimensional computational fluid dynamics inlet flow profiles. Once $p^+$ is estimated, the blood flow inside the portal vein (304 in FIG. 3) is computed using the three-dimensional computational fluid dynamics solver. The effect of heat on the viscosity of the flow may be neglected. As a result, the flow related computation to simulate the blood flow in the liver can be performed before the simulation of heat diffusion.

Returning to FIG. 1, at step 110, heat diffusion in the liver due to ablation is simulated based on the simulated blood flow and the location of the virtual ablation probe. The diffusion of heat over time in the liver tissue is simulated by calculating the diffusion or progression of temperature change over time. A temperature distribution field is solved as a function of time using a partial differential equation or other equation. The numerical solution of the bio-heat transfer equations yields an underlying temperature distribution field that varies in space and time. Computing heat diffusion in biological tissue amounts to solving the coupled bio-heat equations derived from the theory of porous media, where each elementary volume is assumed to comprise a tissue fraction and a blood fraction. Two main simplifications for solving the coupled bio-heat equations are the Pennes model and the Wulff-Klinger (WK) model.

In the Pennes model, the blood temperature is assumed constant, which holds close to large vessels, where blood velocity is high. The Pennes model may be expressed as:

$$(1-\epsilon)p_tc_t(\delta T_t/\delta t)=(1-\epsilon)Q+(1-\epsilon)del\cdot(d_tdel\cdot T_t)+H(T_{b0}-T_t). \quad (1)$$

In the Wulff-Klinger model, equilibrium between tissue and blood temperatures is assumed (Tt=Tb). This model is therefore well-suited small vessels, where blood velocity is low. The Wulff-Klinger model can be expressed as:

$$(1-\epsilon)p_tc_t(\delta T_t/\delta t)=(1-\epsilon)Q+(1-\epsilon)del\cdot(d_tdel\cdot T_t)-\epsilon p_bc_bv\cdot del\cdot T_t. \quad (2)$$

In both equations, T is the temperature, Q is the source term and v is the blood velocity. Subscripts t and b refer to tissue and blood phases respectively. $T_{b0}$ is the mean temperature, which is assumed to be constant, of the blood in the portal and hepatic veins. Definitions and exemplary values of the remaining model parameters are provided in Table 1, below.

TABLE 1

Values of the parameters used in the simulation

| parameter | description | value |
|---|---|---|
| $\rho_b \cdot \rho_t$ | blood and tissue donation | $1.06 \times 10^3$ kg m$^{-3}$ |
| $c_b$ | blood heat capacity | $4.18 \times 10^3$ J(kg K)$^{-1}$ |
| $c_t$ | tissue heat capacity | $3.6 \times 10^3$ J(kg K)$^{-1}$ |
| $c_t^*$ | tissue heat capacity in dead cells | $0.67 \times 10^3$ J(kg K)$^{-1}$ |
| $d_b \cdot d_t$ | blood and tissue heat conductivities | $0.512 \times (1 + 0.00161 \times (T - 310))$ W(m K)$^{-1}$ |
| H | connective transfer coefficient | $24.4 \times 10^4$ W (m$^3$ K)$^{-1}$ |
| $\epsilon$ | blood volume fraction | 0.1 |
| $\kappa$ | permeability | $2.0 \times 10^{-2}$ m$^2$ |
| $\mu$ | dynamic viscosity | $4.6 \times (2.414 \times 10^{-5} \times 10^{247.8/(T - 140)})_{Pas}$ |
| $k_f$ | forward rate constant | $3.33 \times 10^{-3}$ s$^{-1}$ |
| $k_b$ | backward rate constant | $7.77 \times 10^{-3}$ s$^{-1}$ |
| $T_k$ | parameter of cell state model | 40.5° C. |

The main difference between the Pennes and the Wulff-Klinger models lies in their cooling terms (i.e., the last term of the right-hand side). The former acts as a volumetric homogeneous heat sink whilst the latter accounts for the directional effect of blood flow on the tissue temperature field. Therefore, both equations can be easily implemented in a modular way to cope with tissue inhomogeneity, by using one or the other cooling term.

Current imaging techniques may not allow estimation of an accurate ratio between blood and liver tissue. Large vessels are clearly identified in the patient-specific anatomical model of the liver, but small capillaries are difficult to image. Therefore embodiments of the present invention solve the bio-heat equation by combining the Pennes and Wulff-Klinger models in a unified and modular framework to model large and small vessels. Assuming that blood vessels and the surrounding tissue are isolated from each other, the liver temperature $T_t$ is solved using the diffusion equation $p_tc_t(\delta T_t/\delta t)=Q+del\cdot(d_tdel\cdot T_t)$ everywhere in the tetrahedral domain (i.e., everywhere in the domain of the patient-specific anatomical model). The cooling term $H(Tb0-Tt)/(1-\epsilon)$ is added when a tetrahedron belongs to a large vessel or artery (Pennes model) and the cooling term $\epsilon p_bc_bv\cdot del\cdot T_t$ is added when the tetrahedron belongs to a small vessel or the parenchyma (Wulff-Klinger model).

The bio-heat and porous media models are solved using a finite element method (FEM). Test functions defined on linear tetrahedral elements, for instance, are used to discretize a weak form of the bio-heat equation (e.g., Garlekin's method). As a result, the heat diffusion is obtained by solving a linear system at every time step. Efficient implicit schemes may be used to have unconditional numerical stability, thus enabling large time steps for increased computational efficiency. A pre-requisite for FEM is the availability of detailed 3D tetrahedral, other meshes, or sampling of patient's liver. Once the anatomical model is generated, a virtual probe is placed and ablation is simulated using FEM.

In one example implementation of the finite element method on a tetrahedral mesh, the discretized equation: M$\ddot{U}$+KU=B is solved, with U the temperature, M the mass matrix, K the stiffness matrix for the diffusion, the reaction and the advection part, and B the vector including boundary conditions. Diffusion, reaction and advection terms are implemented in a modular way, but may be combined. Neumann boundary conditions are used at the organ boundary. The heat source term can be modeled through a Dirichlet boundary condition of 100° C. at the location of the virtual probe. The blood going through the liver is treated as a constant temperature of 37° C. For the advection term, a three-dimensional characteristic Galerkin scheme is used for numerical stability. First-order implicit Euler time discretization is employed. The resulting matrix system Ax=B is solved using the conjugate gradient iterative algorithm. For the computational fluid dynamics, a full 3D Navier-Stokes viscous solver, expressed in an Eulerian framework which embeds the domain boundary using a level set representation of the segmented vessel is used.

Returning to FIG. 1, at step 112, cellular necrosis in the liver is simulated based on the simulated heat diffusion. Heat from an ablation probe can cause cellular necrosis in the liver. In one embodiment, the tissue damage is modeled as using a three state model. The model computes the variation of concentration of live cells (A), vulnerable cells (C), and dead cells (D) over time according to the state equation:

$$A \underset{k_b}{\overset{k_f}{\rightleftarrows}} V \overset{k_f}{\rightarrow} D$$

where $k_f$ and $k_b$ are the rates of cell damage and recovery, respectively. In particular, $k_f$ depends on the temperature through the equation: $k_f = k_f^- e^{T/T_k}$ (1 A) with $k_f^-$ being a scaling constant and $T_k$ a parameter that sets the rate of the exponential increase with temperature. This equation results in three simultaneous ordinary differential equations, solved at each node of the computational domain, yielding spatially-varying cell state field. Any temporal integration scheme may be used (e.g., first order Euler explicit or first order Euler implicit). In an exemplary implementation, the initial conditions can be chosen as A=0.99, V=0.01 and D=0.00. Exemplary values for the parameters, $k_b$, $k_f^-$, and $T_k$ are shown in Table 1, above. Additionally, dead or damaged cells do not have the same heat capacity ct as live cells. This phenomenon can affect heat transfer and ablation extent. Accordingly, at each time step of the computation, the stated of the cell is updated at each point in the patient-specific anatomical model of the liver, given the cell's current temperature. The corresponding heat capacity ct is used if healthy or vulnerable, dead cells have a fixed heat capacity of $c_t^*$.

Other cell death models may be used as well. For example, in another embodiment, the tissue damage can be modeled using a survival fraction index and an Arrhenius-like equation. The tissue damage model is experimentally determined, extracted from studies, or created from theory. The survival fraction index indicates the amount of live versus dead cells in a region as a function of temperature. The survival fraction index is, calculated from the current temperature using an Arrhenius-like model. More precisely, the survival fraction index is the ratio of viable cells to the total number of cells in a region of interest. When the survival fraction index is <<1, cells in this spatial region are dead. The Arrhenius equation models the relationship of the survival fraction with respect to temperature.

Figure 4:
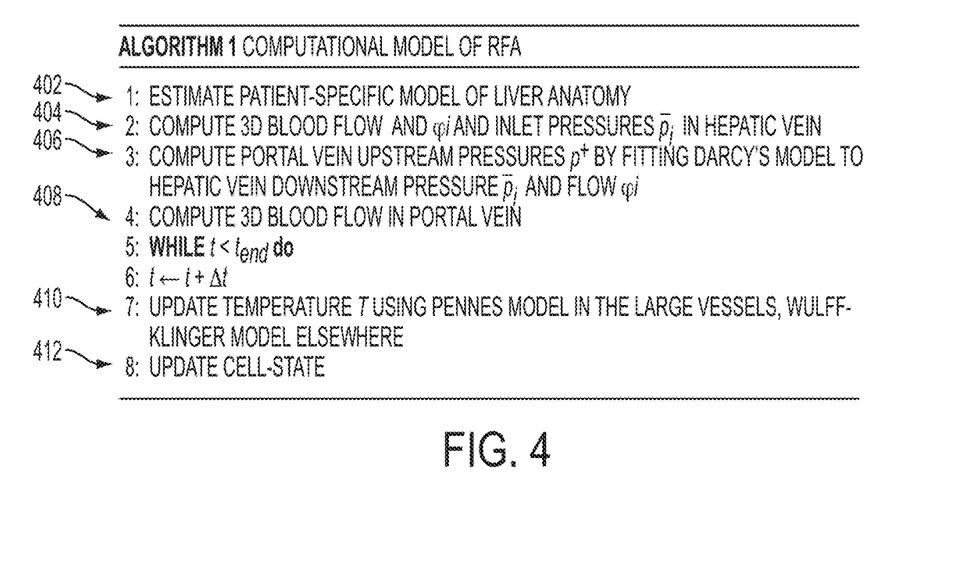
FIG. 4 illustrates an algorithm for implementing a computational model for simulating radio frequency ablation (ABA), according to an embodiment of the present invention.

FIG. 4 illustrates an algorithm for implementing a computational model for simulating radio frequency ablation (ABA), according to an embodiment of the present invention. The algorithm of FIG. 4 can be used to implement steps 106-112 of FIG. 1. As illustrated in FIG. 4, at 402, the patient-specific model of liver anatomy is estimated. At 404, compute 3D blood flow φi and inlet pressures p in hepatic vein are computed. At 406, portal vein upstream pressure p+ is computed by fitting Darcy's model to the hepatic vein downstream pressures p and flow φi. At 408, 3D blood flow in portal vein is computed. The blood flow and pressures in the hepatic vein and the portal vein provide Dirichlet boundary conditions for computing the blood velocity inside the parenchyma. Once the blood flow is simulated in the whole patient-specific model of the liver, operations 410 and 412 are performed at each time step (t) between while t<$t_{end}$. At 410, the temperature T using Pennes model in the large vessels and Wulff-Klinger model elsewhere (e.g., parenchyma). At 412, the cell-state is updated by using the cellular necrosis model based on the simulated temperature.

Returning to FIG. 1, at step 114 temperature maps and a visualization of a simulated necrosis area are output. For example, the temperature maps and simulated necrosis area visualization can be output by displaying the temperature maps and simulated necrosis area visualization on a display of a computer system.

Figure 5:
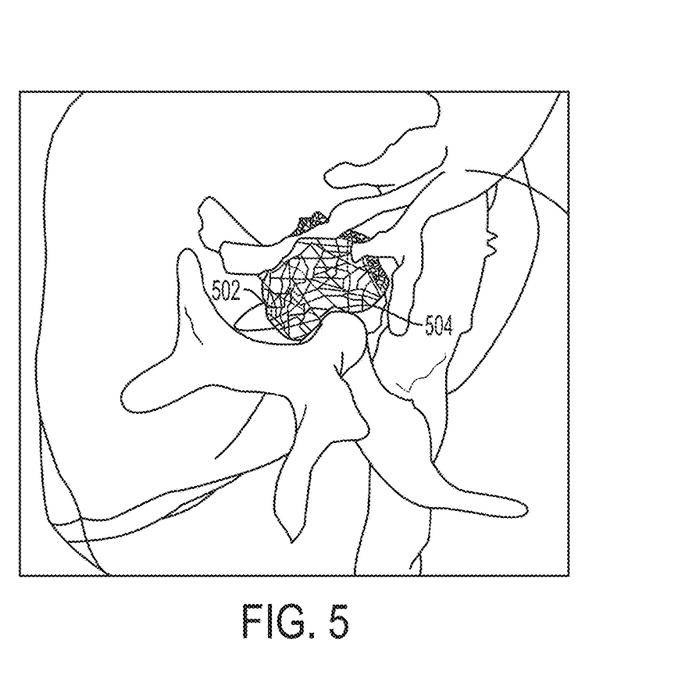
FIG. 5 illustrates an exemplary visualization of a simulated necrosis area.

The proposed framework has been evaluated on one patient-specific geometry extracted from pre-operative CT images. The virtual probe is placed in within the middle of the tumor. Cells within a sphere around the probe tip are heated at 100° C. to mimic the topology of the probe. The protocol to be clinically used is simulated as: heating for 10 minutes, stopping the heating for the next 5 minutes, and repeat the process by increasing the sphere diameter from 10 mm to 20 mm and finally 30 mm. Using the Pennes Model, the model is able to predict the cooling effect of the big veins. The distribution of the temperature over the liver and a simulated necrosis area are returned. FIG. 5 illustrates an exemplary visualization of a simulated necrosis area. As shown in FIG. 5, the simulated necrosis area 502 is visualized by visualizing all portions of the tetrahedral mesh having a dead cell state. Alternatively, necrotic areas can be visualized using iso-contours of the survival fraction index. A ground truth cellular necrosis area 504 from a post-operative MRI is overlaid for comparison. As can be seen in FIG. 5, the predicted necrotic extent from the simulated necrosis area 502 qualitatively agrees with the ground truth cellular necrosis 504 that is actually observed in the patient.

Figure 6:
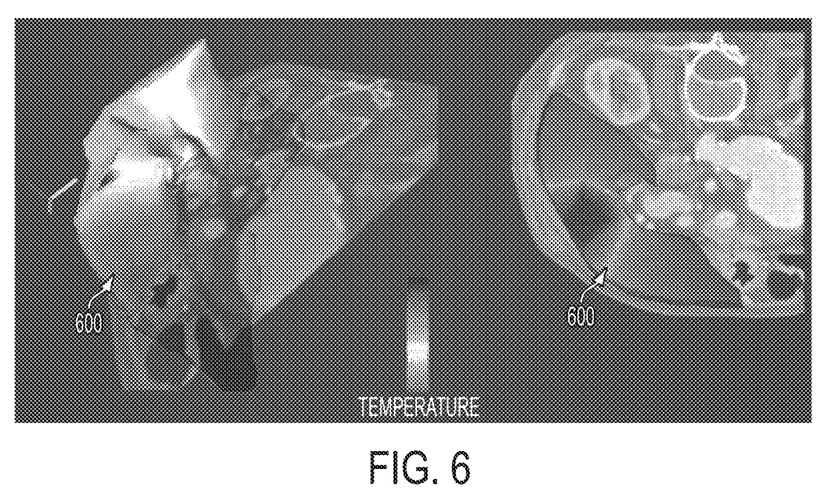
FIG. 6 illustrates an exemplary temperature map.

The temperature maps show the spatial and temporal variation of the temperature in the liver over time. In one embodiment, the liver temperature can be visualized using color maps and isothermal contours that indicate the heat of particular regions in the liver. FIG. 6 illustrates an exemplary temperature map. As shown in FIG. 6, a temperature map 600 showing temperature at a time step in the simulation is mapped to CT cross-section images.

Figure 7:
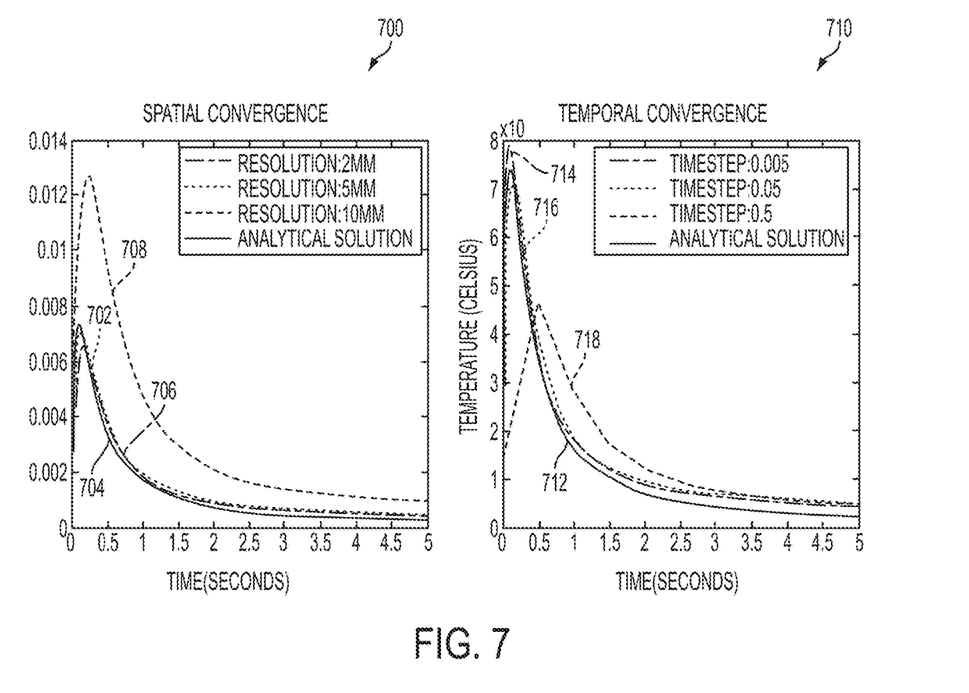
FIG. 7 illustrates analysis of spatial and temporal simulation results compared to an analytical solution.

The present inventors evaluated the computational model for simulating radiofrequency ablation in the liver by comparing its behavior on a regular tetrahedral beam mesh where the 3D analytical solution of an instantaneous point source of mass M released at location $p_0=(x_0,y_0,z_0)$ and time $t_0$ with v=(u,v,w) f the advection-diffusion equation $\partial T/\partial T + v \cdot \nabla T = \nabla (a \nabla T)$ is known:

$$T(p, t) = \frac{M}{[4\pi(t-t_0)d]^{3/2}} \exp\left[-\frac{\|p - p_0 - (t-t_0)v\|^2}{4d(t-t_0)}\right].$$

The following values were used: M(° C./mm³)=100, d(mm²/s)=100, $t_0$=0 s, and v(mm/s)=(0.001,0,0) (values of the same order of magnitude as for the patient simulation). The source term is set at the center of the mesh to minimize the effects of the boundary conditions. At time t=0 s, the temperature values were initialized at each vertex with the analytical solution at time t=0.05 s, and the temperature was analyzed at several points of the mesh. FIG. 7 illustrates analysis of spatial and temporal convergence of simulation results compared to the analytical solution. Image 700 shows spatial convergence analysis comparing temperature values of the analytical solution 702 over time with temperature values calculated using simulations with mesh resolutions of 2 mm (704), 5 mm (706), and 10 mm (708). Image 710 shows temporal convergence analysis comparing temperature values of the analytical solution 712 over time with temperature values calculated using simulations with time steps of 0.005 s (714), 0.05 s (716), and 0.5 s (718). As expected, the more accurate smaller the time step and spatial resolution of the mesh, the more accurate the simulated solution is compared to the analytical solution. As shown in FIG. 7, a time step of 0.5 s and a resolution of 5 mm provides a good compromise between accuracy and computational cost.

Embodiments of the present invention provide a patient-specific model for simulating liver tumor ablation. Embodiments of the present invention simulate heat propagation and cellular necrosis based on patient-specific anatomic model estimated from medical image data of the patient, and takes into account the heat sink effect of blood vessels and porous circulation in the liver. Embodiments of the present invention provide visualization of temperature distribution, and thus lesion propagation, as well as cellular necrosis, allowing for improved planning and guidance for liver tumor ablation procedures.

In a possible implementation, an optimal probe location may be automatically determined using the above described simulation framework. Rather than rely on user feed back, the temperature diffusion and corresponding necrosis associated with different locations and/or other variance in ablation can be compared to the region to be treated. For example, the position, power level, and sequence of application resulting in the greatest, sufficient, or complete coverage of the tumor and least necrosis of healthy tissue may be found by simulating different combinations. By successively computing the thermal dose for a number of needle placements, the placement with maximum coverage on the tumor can be found. In a successive optimization loop to solve for the probe location, orientation, and/or other characteristic, the combination for maximum tumor thermal dose coverage is found. The thermal dose coverage may be measured as the area defined by temperatures higher than a threshold (e.g., 70 degrees Celsius). Other measures may be used, such as a weighted measure that most strongly weights necrosis of the tumor while considering avoidance of necrosis outside the tumor.

Figure 8:
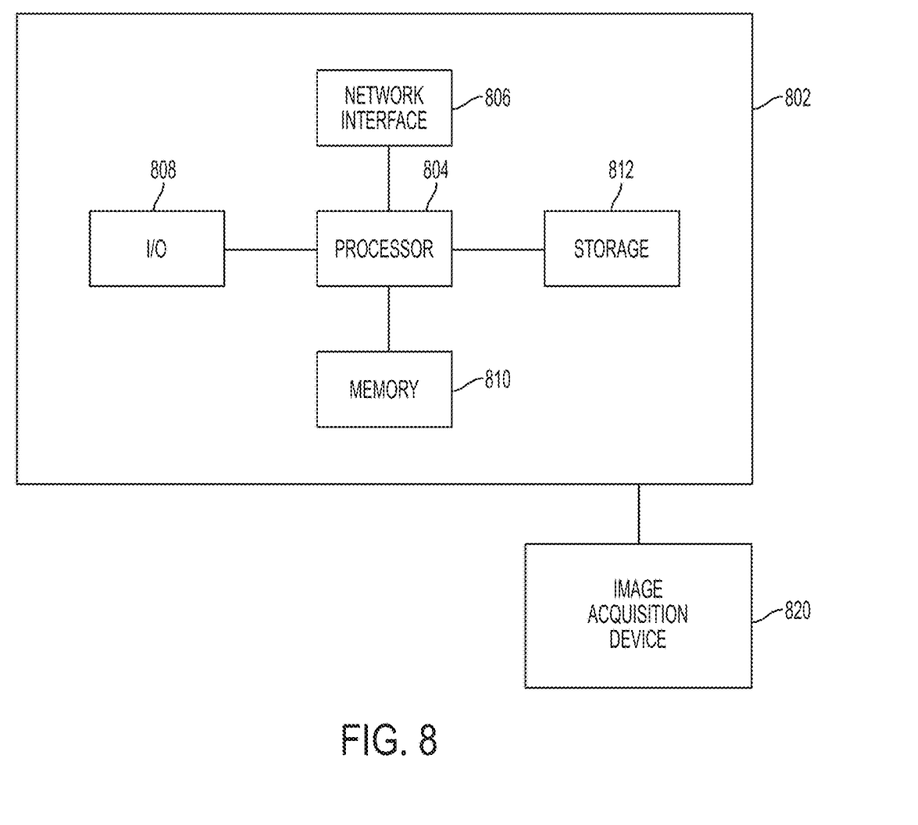
FIG. 8 is a high-level block diagram of a computer capable of implementing the present invention.

The above-described methods for patient-specific modeling and simulation of liver tumor ablation can be implemented on a computer using well-known computer processors, memory units, storage devices, computer software, and other components. A high-level block diagram of such a computer is illustrated in FIG. 8. Computer 802 contains a processor 804, which controls the overall operation of the computer 802 by executing computer program instructions which define such operation. The computer program instructions may be stored in a storage device 812 (e.g., magnetic disk) and loaded into memory 810 when execution of the computer program instructions is desired. Thus, the steps of the methods of FIGS. 1 and 4 may be defined by the computer program instructions stored in the memory 810 and/or storage 812 and controlled by the processor 804 executing the computer program instructions. An image acquisition device 820, such as a CT scanning device, C-arm image acquisition device, MR scanning device, Ultrasound device, etc., can be connected to the computer 802 to input image data to the computer 802. It is possible to implement the image acquisition device 820 and the computer 802 as one device. It is also possible that the image acquisition device 820 and the computer 802 communicate wirelessly through a network. The computer 802 also includes one or more network interfaces 806 for communicating with other devices via a network. The computer 802 also includes other input/output devices 808 that enable user interaction with the computer 802 (e.g., display, keyboard, mouse, speakers, buttons, etc.). Such input/output devices 808 may be used in conjunction with a set of computer programs as an annotation tool to annotate volumes received from the image acquisition device 820. One skilled in the art will recognize that an implementation of an actual computer could contain other components as well, and that FIG. 8 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for planning and guidance of tumor ablation therapy in a target organ based on a patient-specific model, comprising:

generating a patient-specific anatomical model of the target organ and a circulatory system of the target organ from medical image data of a patient, wherein generating the patient-specific anatomical model of the target organ and the circulatory system of the target organ comprises generating a patient-specific anatomical model of the liver including a liver parenchyma, at least one tumor, a hepatic vein, a portal vein, and at least one artery by segmenting the liver parenchyma, the at least one tumor, the hepatic vein, the portal vein, and the at least one artery in the medical image;

simulating blood flow in vessels and porous regions of the target organ based on the patient-specific anatomical model by:

calculating 3D blood flow and inlet pressures in the hepatic vein over a plurality of time steps using computational fluid dynamics (CFD) simulation, calculating portal vein and artery upstream pressures over the plurality of time steps based on the blood flow and the inlet pressures in the hepatic vein, and calculating 3D blood flow in the portal vein and the at least one artery over the plurality of time steps based on the portal vein upstream pressures using CFD simulation;

simulating heat diffusion due to ablation based on a virtual ablation probe position and operating parameters and the simulated blood flow in the vessels and porous regions of the target organ considering both cooling effects from the blood flow in the vessels and the porous tissue blood perfusion by calculating, for each of a plurality of points in the patient-specific anatomical model, a temperature at each of the plurality of time steps using a first bio-heat equation having a first cooling term if the point belongs to a vessel or an artery, and a second bio-heat equation having a second cooling term if the point belongs to a porous medium;

simulating cellular necrosis in the target organ based on the simulated heat diffusion; and generating a patient-specific visualization of a necrosis region in the anatomical model resulting from the simulation of heat diffusion due to ablation and the simulation of the cellular necrosis in the target organ.

2. The method of claim 1, wherein generating a patient-specific anatomical model of the liver including a liver parenchyma, at least one tumor, a hepatic vein, a portal vein, and at least one artery comprises:

individually segmenting each of the liver parenchyma, the at least one tumor, the hepatic vein, the portal vein, and the at least one artery in the medical image using random walker segmentation;

merging the segmented liver parenchyma, at least one tumor, hepatic vein, portal vein, and the at least one artery into a multi-label mask image; and generating a tetrahedral mesh based on the multi-label mask image.

3. The method of claim 1, wherein the first bio-heat equation is a Pennes-type model bio-heat equation and the second bio-heat equation is a Wulff-Klinger-type model bio-heat equation.

4. The method of claim 1, wherein calculating, for each of a plurality of points in the patient-specific anatomical model, a temperature at each of a plurality of time steps using a first bio-heat equation having a first cooling term if the point belongs to a vessel or an artery, and a second bio-heat equation having a second cooling term if the point belongs to a porous medium comprises:

if the point belongs to a vessel or an artery, calculating the temperature at each of the plurality of time steps by solving $p_t c_t \partial T_t / \partial t = Q + \nabla \cdot (d_t \nabla_t) + H(T_{b0} - T_t)/(1-\epsilon)$; and if the point belongs to a porous medium, calculating the temperature at each of the plurality of time steps by solving $p_t c_t \partial T_t / \partial t = Q + \nabla \cdot (d_t \nabla_t) - \epsilon p_b c_b v \cdot \nabla T_t /(1-\epsilon)$, where $T_t$ is the temperature at time step t, Q is a source term representing heat applied by the virtual ablation probe at the virtual ablation probe position and operating parameters, v is blood velocity determined from the simulated blood flow, $T_{b0}$ is a mean temperature of blood in the vessels and arteries, $p_t$ and $p_b$ are tissue and blood densities, respectively, $c_t$ and $c_b$ are heat capacities of tissue and blood, respectively, $d_t$ is a tissue heat conductivity, H is a convective transfer coefficient, and $\epsilon$ is a blood volume fraction.

5. The method of claim 1, wherein calculating, for each of a plurality of points in the patient-specific anatomical model, a temperature at each of a plurality of time steps using a first bio-heat equation having a first cooling term if the point belongs to a vessel or an artery, and a second bio-heat equation having a second cooling term if the point belongs to a porous medium comprises:

if the point belongs to the hepatic vein, the portal vein, or the at least one artery, calculating the temperature at each of the plurality of time steps using the first bio-heat equation; and if the point belongs to the liver parenchyma, calculating the temperature at each of the plurality of time steps using the second bio-heat equation.

6. The method of claim 1, wherein a heat diffusion map resulting from simulating the heat diffusion is adjusted so that temperatures at plurality of locations in the heat diffusion map over time match to actual acquired temperatures at corresponding locations.

7. The method of claim 1, wherein the heat diffusion is simulated at each of the plurality of time steps, and simulating cellular necrosis in the target organ based on the simulated heat diffusion comprises:

calculating a variation of a concentration of alive cells, vulnerable cells, and dead cells in the target organ over the plurality of time steps based on the simulated heat diffusion.

8. The method of claim 7, wherein calculating a variation of a concentration of alive cells, vulnerable cells, and dead cells in the target organ over the plurality of time steps based on the simulated heat diffusion comprises:

at each time step:
calculating a cell damage rate based on temperatures generated by the simulated heat diffusion at that time step; and calculating the concentration of alive cells, vulnerable cells, and dead cells in the target organ based on the cell damage rate, a cell recovery rate, and a previous concentration of alive cells, vulnerable cells, and dead cells in the target organ.

9. The method of claim 8, wherein simulating cellular necrosis in the target organ based on the simulated heat diffusion further comprises:

at each time step, updating at least one tissue parameter of a bio-heat model used for simulating the heat diffusion based on the concentration of alive cells, vulnerable cells, and dead cells in the target organ calculated at that time step, prior to simulating the heat diffusion at the a next time step.

10. The method of claim 1, further comprising:
generating a visualization of a temperature map showing the simulated heat diffusion in the target organ.

11. The method of claim 1, wherein simulating blood flow in vessels and porous regions of the target organ based on the patient-specific anatomical model further comprises:

simulating blood flow in the liver parenchyma using inlet pressures at hepatic vein tips and outlet pressures at portal vein tips resulting from the CFD simulations in the hepatic vein and the portal vein as boundary conditions.

12. An apparatus for planning and guidance of tumor ablation therapy in a target organ based on a patient-specific model, comprising:

a processor; and
a memory storing computer program instructions, which when executed by the processor cause the processor to perform operations comprising:

generating a patient-specific anatomical model of the target organ and a circulatory system of the target organ from medical image data of a patient, wherein generating the patient-specific anatomical model of the target organ and the circulatory system of the target organ comprises generating a patient-specific anatomical model of the liver including a liver parenchyma, at least one tumor, a hepatic vein, a portal vein, and at least one artery by segmenting the liver parenchyma, the at least one tumor, the hepatic vein, the portal vein, and the at least one artery in the medical image;

simulating blood flow in vessels and porous regions of the target organ based on the patient-specific anatomical model by:

calculating 3D blood flow and inlet pressures in the hepatic vein over a plurality of time steps using computational fluid dynamics (CFD) simulation, calculating portal vein and artery upstream pressures over the plurality of time steps based on the blood flow and the inlet pressures in the hepatic vein, and calculating 3D blood flow in the portal vein and the at least one artery over the plurality of time steps based on the portal vein upstream pressures using CFD simulation;

simulating heat diffusion due to ablation based on a virtual ablation probe position and operating parameters and the simulated blood flow in the vessels and porous regions of the target organ considering both cooling effects from the blood flow in the vessels and the porous tissue blood perfusion by calculating, for each of a plurality of points in the patient-specific anatomical model, a temperature at each of the plurality of time steps using a first bio-heat equation having a first cooling term if the point belongs to a vessel or an artery, and a second bio-heat equation having a second cooling term if the point belongs to a porous medium;

simulating cellular necrosis in the target organ based on the simulated heat diffusion; and generating a patient-specific visualization of a necrosis region in the anatomical model resulting from the simulation of heat diffusion due to ablation and the simulation of the cellular necrosis in the target organ.

13. The apparatus of claim 12, wherein the first bio-heat equation is a Pennes-type model bio-heat equation and the second bio-heat equation is a Wulff-Klinger-type model bio-heat equation.

14. The apparatus of claim 12, wherein the heat diffusion is simulated at each of the plurality of time steps, and simulating cellular necrosis in the target organ based on the simulated heat diffusion comprises:

calculating a variation of a concentration of alive cells, vulnerable cells, and dead cells in the target organ over the plurality of time steps based on the simulated heat diffusion.

15. The apparatus of claim 14, wherein calculating a variation of a concentration of alive cells, vulnerable cells, and dead cells in the target organ over the plurality of time steps based on the simulated heat diffusion comprises:

calculating a cell damage rate at each time step based on temperatures generated by the simulated heat diffusion at that time step; and calculating the concentration of alive cells, vulnerable cells, and dead cells in the target organ at each time step based on the cell damage rate, a cell recovery rate, and a previous concentration of alive cells, vulnerable cells, and dead cells in the target organ.

16. The apparatus of claim 15, wherein simulating cellular necrosis in the target organ based on the simulated heat diffusion further comprises:

updating at least one tissue parameter of a bio-heat model used for simulating the heat diffusion based on the concentration of alive cells, vulnerable cells, and dead cells in the liver calculated at each time step, prior to simulating the heat diffusion at the a next time step.

17. The apparatus of claim 12, wherein the operations further comprise:

generating a visualization of a temperature map showing the simulated heat diffusion in the target organ.

18. A non-transitory computer readable medium storing computer program instructions for planning and guidance of tumor ablation therapy in a target organ based on a patient-specific model, the computer program instructions when executed by a processor cause the processor to perform operations comprising:

generating a patient-specific anatomical model of the target organ and a circulatory system of the target organ from medical image data of a patient, wherein generating the patient-specific anatomical model of the target organ and the circulatory system of the target organ comprises generating a patient-specific anatomical model of the liver including a liver parenchyma, at least one tumor, a hepatic vein, a portal vein, and at least one artery by segmenting the liver parenchyma, the at least one tumor, the hepatic vein, the portal vein, and the at least one artery in the medical image;

simulating blood flow in vessels and porous regions of the target organ based on the patient-specific anatomical model by:

calculating 3D blood flow and inlet pressures in the hepatic vein over a plurality of time steps using computational fluid dynamics (CFD) simulation, calculating portal vein and artery upstream pressures over the plurality of time steps based on the blood flow and the inlet pressures in the hepatic vein, and calculating 3D blood flow in the portal vein and the at least one artery over the plurality of time steps based on the portal vein upstream pressures using CFD simulation;

simulating heat diffusion due to ablation based on a virtual ablation probe position and operating parameters and the simulated blood flow in the vessels and porous regions of the target organ considering both cooling effects from the blood flow in the vessels and the porous tissue blood perfusion by calculating, for each of a plurality of points in the patient-specific anatomical model, a temperature at each of the plurality of time steps using a first bio-heat equation having a first cooling term if the point belongs to a vessel or an artery, and a second bio-heat equation having a second cooling term if the point belongs to a porous medium;

simulating cellular necrosis in the target organ based on the simulated heat diffusion; and generating a patient-specific visualization of a necrosis region in the anatomical model resulting from the simulation of heat diffusion due to ablation and the simulation of the cellular necrosis in the target organ.

19. The non-transitory computer readable medium of claim 18, wherein the first bio-heat equation is a Pennes-type model bio-heat equation and the second bio-heat equation is a Wulff-Klinger-type model bio-heat equation.

20. The non-transitory computer readable medium of claim 18, wherein calculating, for each of a plurality of points in the patient-specific anatomical model, a temperature at each of a plurality of time steps using a first bio-heat equation having a first cooling term if the point belongs to a vessel or an artery, and a second bio-heat equation having a second cooling term if the point belongs to a porous medium comprises:

if the point belongs to a vessel or an artery, calculating the temperature at each of the plurality of time steps by solving $p_t c_t \partial T_t/\partial t = Q + \nabla \cdot (d_t \nabla T_t) + H(T_{b0} - T_t)/(1-\epsilon)$; and if the point belongs to a porous medium, calculating the temperature at each of the plurality of time steps by solving $p_t c_t \partial T_t/\partial t = Q + \nabla \cdot (d_t \nabla T_t) - \epsilon p_b c_b v \cdot \nabla T_t/(1-\epsilon)$, where $T_t$ is the temperature at time step t, Q is a source term representing heat applied by the virtual ablation probe at the virtual ablation probe position and operating parameters, v is blood velocity determined from the simulated blood flow, $T_{b0}$ is a mean temperature of blood in the vessels and arteries, $p_t$ and $p_b$ are tissue and blood densities, respectively, $c_t$ and $c_b$ are heat capacities of tissue and blood, respectively, $d_t$ is a tissue heat conductivity, H is a convective transfer coefficient, and $\epsilon$ is a blood volume fraction.

21. The non-transitory computer readable medium of claim 18, wherein calculating, for each of a plurality of points in the patient-specific anatomical model, a temperature at each of a plurality of time steps using a first bio-heat equation having a first cooling term if the point belongs to a vessel or an artery, and a second bio-heat equation having a second cooling term if the point belongs to a porous medium comprises:

if the point belongs to the hepatic vein, the portal vein, or the at least one artery, calculating the temperature at each of the plurality of time steps using the first bio-heat equation; and if the point belongs to the liver parenchyma, calculating the temperature at each of the plurality of time steps using the second bio-heat equation.

22. The non-transitory computer readable medium of claim 18, wherein the heat diffusion is simulated at each of the plurality of time steps, and simulating cellular necrosis in the target organ based on the simulated heat diffusion comprises:

calculating a variation of a concentration of alive cells, vulnerable cells, and dead cells in the target organ over the plurality of time steps based on the simulated heat diffusion.

23. The non-transitory computer readable medium of claim 22, wherein calculating a variation of a concentration of alive cells, vulnerable cells, and dead cells in the target organ over the plurality of time steps based on the simulated heat diffusion comprises:

at each time step:
calculating a cell damage rate based on temperatures generated by the simulated heat diffusion at that time step; and
calculating the concentration of alive cells, vulnerable cells, and dead cells in the target organ based on the cell damage rate, a cell recovery rate, and a previous concentration of alive cells, vulnerable cells, and dead cells in the target organ.

24. The non-transitory computer readable medium of claim 23, wherein simulating cellular necrosis in the target organ based on the simulated heat diffusion further comprises:

at each time step, updating at least one tissue parameter of a bio-heat model used for simulating the heat diffusion based on the concentration of alive cells, vulnerable cells, and dead cells in the target organ calculated at that time step, prior to simulating the heat diffusion at the a next time step.

25. The non-transitory computer readable medium of claim 18, the operations further comprising:

generating a visualization of a temperature map showing the simulated heat diffusion in the target organ.

* * * * *